United States Patent [19]

Dorian

[11] Patent Number: 5,434,057
[45] Date of Patent: Jul. 18, 1995

[54] SPERM MOTILITY ASSAY AND DEVICES

[75] Inventor: Randel Dorian, Orinda, Calif.

[73] Assignee: Quidel Corporation, San Diego, Calif.

[21] Appl. No.: 190,341

[22] Filed: Feb. 2, 1994

[51] Int. Cl.$^6$ .......................... C12Q 1/34; C12Q 1/02; G01N 21/77
[52] U.S. Cl. ........................................ 435/18; 435/29; 435/288; 435/806; 435/975; 422/56; 422/57; 436/169; 436/906
[58] Field of Search ....................... 435/18, 26, 29, 34, 435/288, 805, 808, 810, 969, 970, 975; 422/56, 57; 436/63, 169, 172, 808, 906

[56] References Cited

U.S. PATENT DOCUMENTS

| | | | |
|---|---|---|---|
| 3,814,668 | 6/1974 | Blake et al. | 195/103.5 C |
| 4,147,514 | 4/1979 | Magers et al. | 23/230 B |
| 5,118,630 | 6/1992 | Glaze | 436/65 |

OTHER PUBLICATIONS

Crabbe M., The Development of a Qualitative Assay . . . J. Reprod Fert 51:73–76 (1977).
Aafjes J., Fumarase Activity in Human Ejaculate . . . Andrologia 13(6) 578–582 (1981).
Peleg Y., A Simple Plate-Assay for the Screening . . . Fems Microbio Lett 67:3 233–236 (1990).
Uchijima Y., Studies on Fumarase Activity . . . Japan J Fertil Steril 38(2) 6–10 (1993).
Glass, Robert H., and Ericsson, Ronald J., "Spontaneous Cure of Male Infertility," *Fertility and Sterility*, 31:305–308 (1979).

*Primary Examiner*—William H. Beisner
*Assistant Examiner*—Ralph Gitomer
*Attorney, Agent, or Firm*—Townsend and Townsend Khourie and Crew

[57] ABSTRACT

The present invention provides devices, methods and kits for assessing fertility potential of semen samples. Semen samples may be assayed by the present invention to identify those samples having more than $20 \times 10^6$ motile sperm per milliliter, a concentration associated with fertile samples.

27 Claims, No Drawings

SPERM MOTILITY ASSAY AND DEVICES

BACKGROUND OF THE INVENTION

The present invention provides devices, methods, and kits for convenient determination of male fertility parameters. More specifically, the present invention is able to detect semen samples having a sufficient concentration of motile sperm to support fertility. The devices, methods and kits of the present invention provide easy, one-step assays for such determinations.

Fertility testing is becoming more widespread as increasing numbers of apparently infertile couples seek medical assistance in conception. Because reproductive abnormalities of both sexes may affect fertility, assessing male fertility is common in fertility evaluations.

Male infertility may be due to a number of factors, including hormonal anomalies, work place exposures, and sequelae of infectious diseases. Even common childhood illnesses such as mumps may cause male infertility. Thus, most males are at some risk for infertility and should be evaluated in any fertility work-up.

The most common starting point for evaluation of male fertility is an assessment of the sperm count in semen. The most commonly accepted figure as the lower limit of normal is $20 \times 10^6$ motile sperm per milliliter. Even more important to fertility than absolute sperm count, however, is sperm motility. *Fertility Study*, 31:305 (1979). Therefore, in male fertility analyses sperm motility must also be determined.

Currently available techniques for measuring sperm count and sperm mobility are microscopic in nature. Sperm morphology and motility is visually assessed by laboratory technicians. Because semen evaluation is essentially qualitative, substantial experience is required for accurate evaluation by the technicians. The high level of experience required by laboratory technicians precludes general office evaluation of semen samples and generally requires referral to a reference laboratory. Further, debris in semen samples can cause erroneous or inconsistent results.

Accurate assessment of sperm motility also requires that the semen sample be fresh. Since the sample must be analyzed by a reference laboratory, the sample must usually be obtained at the laboratory. Often this requires additional appointments at medical facilities and time away from work. This can be inconvenient for many patients and even a hardship for patients living in rural areas far away from reference laboratories.

Attempts to develop biochemical assays of semen have not resulted in simple procedures which may be performed in the physician's office. Most biochemical markers have failed to demonstrate correlations with either sperm number or motility. Fumarase activity, an enzyme present in semen, has been found to correlate to both sperm count and percentage motility. Crabbe, *J. Reprod. Fert.*, 51:73–76 (1977). Crabbe measured fumarase activity by spectrophotometric measurements. Unfortunately, spectrophotometric assays are not generally suitable for office assays because of the cost of these specialized devices as well as the training required for accurate and reproducible operation.

What is needed in the art is a simple assay for assessing sperm count and motility that does not require expensive specialized instrumentation or extensive training. One step assays that could be performed according to easy to follow instructions without specialized training would be optimal. Surprisingly, the present invention satisfies these and other needs.

SUMMARY OF THE INVENTION

The present invention provides devices for assessing sperm number and motility in semen samples. The devices comprise a solid support having a carrier matrix containing a fumarase substrate and malate dehydrogenase. Generally, the fumarase substrate will be fumaric acid, a fumarate salt, or a fumarate ester. Conveniently, the device is provided in a dipstick form.

Also provided are methods for identifying a semen sample having more than about $20 \times 10^6$ mobile sperm per milliliter. The methods generally comprise applying the sample to a carrier matrix on a solid support, which carrier matrix contains a fumarase substrate and malate dehydrogenase; and detecting a visual signal from the solid support resulting from metabolism of the fumarase substrate by fumarase present in the sample. Similar to the devices above, the fumarase substrate will generally be fumaric acid, a fumarate salt, or a fumarate ester. Often, the visual signal will be a color change that may be detected visually or by an instrument. Typically, the visual signal will be detected within 10 minutes of applying the sample to the carrier matrix.

Kits for the detection of semen samples containing more than about $20 \times 10^6$ motile sperm cells per milliliter are also provided by the present invention. The kits include devices of the present invention and semen collection vials. Instruments to detect the visual signal or reference color charts may also be included in the kits.

DESCRIPTION OF SPECIFIC EMBODIMENTS

The present invention provides convenient assays for detection of motile sperm in a semen sample. As noted above, fumarase enzyme activity has been correlated with the concentration of viable, motile sperm in a semen sample. The assays quantitatively detect fumarase enzyme in the sample. The assays of the present invention may be constructed on a dipstick which provides a one-step method of analysis. Generally, fumarase activity is assessed by a color change on the dipstick. The assay is rapid, easy to use with little training, and can be performed in the clinician's office.

Fumarase enzyme converts fumaric acid to malic acid. Fumarase also converts fumarate salts and esters to malic acid. Hereinafter, fumaric acid will be understood to include fumarate salts and fumarate esters. The assay provides fumaric acid in a carrier matrix. The fumaric acid is typically supplied in excess in the carrier matrix so that formula fumarase activity will be rate limiting. The conversion of fumaric acid to malic acid is coupled to a system that will generate a visual signal. The visual signal will provide a quantitative assessment of the fumarase activity in the sample. The fumarate substrate coupling of the generation of the visual signal to reduction to malic acids generally occurs as outlined below:

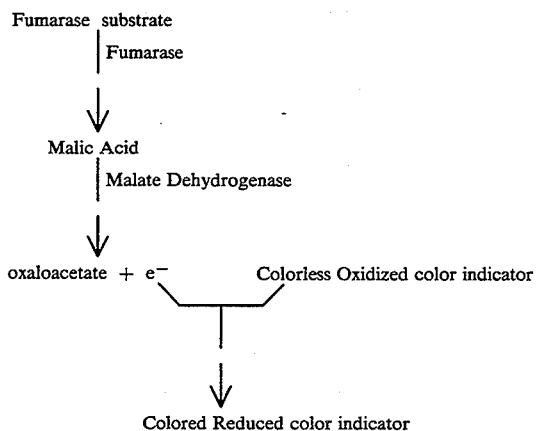

Generally, the color generating system will be a nicotinamide adenine dinucleotide (NADH) dehydrogenase system capable of reducing a dye to create a color change. Preferably, malic dehydrogenase is present in the carrier matrix. The malic dehydrogenase converts malic acid to oxaloacetate and reduces NAD+ to NADH. The NADH couples the reaction to reduction of a tetrazolium salt. The tetrazolium salt is reduced using phenazine methosulfate as an electron acceptor. Reduction of the tetrazolium salt produces formazan which has a blue color. Appearance of the blue color in the assay indicates that sufficient fumarase was present in the sample to correlate with a motile sperm concentration associated with fertility. Persons of skill will appreciate that other reducing systems and dyes may be employed in the present invention.

One aspect of the present invention are devices for assessing sperm motility in semen samples. Typically the devices comprise a solid support having a carrier matrix containing a fumarase substrate and malic dehydrogenase. The devices are capable of differentiating semen samples that have more than about $20 \times 10^6$ motile sperm per milliliter from semen samples having fewer than about $20 \times 10^6$ motile sperm per milliliter. Because this concentration of motile sperm is generally indicative of fertile semen, the devices of the present application provide a means for identifying both adequate absolute sperm count and motile sperm count in semen samples.

The devices of the present invention include a solid support. The solid support provides a convenient platform for performance of the assay. The composition and shape of the solid support are not critical and may vary. Typically, the solid support is a plastic or nylon dipstick. The dipstick will usually be semi-rigid. In embodiments configured as a dipstick, the carrier matrix will generally be located on one end of the dipstick. Alternatively, the solid support may be shaped so that semen samples may be applied to the device by means other than dipping, e.g., application of controlled amounts of semen by pipettes or the like.

The solid support has a carrier matrix. The carrier matrix may be the whole solid support, a part of the solid support, or a structure attached to the solid support. The carrier matrix will typically be an insoluble bibulous or non-bibulous material that maintains structural integrity when exposed to physiological fluids, such as semen. Suitable bibulous materials include paper, cellulose, synthetic resin fleeces, glass fibers, woven and non-woven fabrics and the like. Suitable non-bibulous matrices include organo-plastic materials such as polystyrene, polypropylene, and the like. Often, the carrier matrix will be a portion of a commercially available filter or a porous membrane. The matrix is generally attached to the solid support by suitable adhesive means, such as double-faced adhesive tape, epoxy resin adhesives, and the like.

The carrier matrices will contain chemical compositions that participate in the chemical assay reactions. Generally, the chemical compositions will be applied to the carrier matrices in solution and dried. In some instances, the chemical compositions may be lyophilized into the carrier matrices. A fumarase substrate will be present in the carrier matrix. The fumarase substrate may be fumaric acid, a fumarate salt, a fumarate ester or the like. Generally, the sodium salt of fumaric acid is employed in the devices of the present invention. Generally the carrier matrices of the present invention have about 10 $\mu$M to about 100 $\mu$M of fumaric acid. Also, because it is desirable that the fumarase concentration in the semen sample be the rate limiting step in the assays of the present invention, the fumaric acid will generally be present in excess amounts.

Also present in the carrier matrix is malic dehydrogenase. Typically, about 0.1 units to 100 units of malic dehydrogenase is in the carrier matrices of the present invention. The malic dehydrogenase will usually be present in excess in the carrier matrices.

In the devices of the present invention, fumarase concentration in the sample will be assessed by a visual signal resulting from conversion of a fumarase substrate to malic acid which is then further metabolized by malic dehydrogenase. The visual signal will generally be produced by chemical reactions coupled to the reduction of malic acid. Compounds participating in these reactions are contained in the carrier matrices.

A preferred system for producing the visual signal is an NADH dehydrogenase system. NAD+ present in the carrier matrix can transfer electrons from the conversion of malic acid to reduce dye compounds. The reduced dyes will have a different optical characteristic than the non-reduced dyes. For example, a colorless tetrazolium salt dye may accept electrons and acquire a blue color in the reduced state. Additional chemical compounds may be required for reduction of the dye. In the above example, phenazone methosulfate and magnesium chloride are required for the reduction of the tetrazolium salt. All of the compounds required for reduction of the dye will be contained in the carrier matrices of the present invention.

Adjuvants which do not participate in any of the chemical test reactions may be also be contained in the carrier matrices. These adjuvants may include thickening agents and enzyme stabilizers. In some instances, the thickening agents will also function as enzyme stabilizers. Suitable thickeners and stabilizers include polyvinylpyrrolidone, sodium alginate, gelatin, bovine serum albumin, polyvinyl alcohol, methylvinyl ether-maleic anhydride polymers, and the like.

Malic acid may be contained in the carrier matrices of some embodiments of the present invention. The malic acid functions to increase the sensitivity of the device by lowering the threshold of malic acid that must be produced by the fumarase to produce detectable color changes.

In devices in which the visual signal is a color change, the solid supports of the devices of the present invention may also have a color indicator panel. The color indicator panel is a reference standard for comparison to the color of the carrier matrix following the assay. The color panel indicator will generally be comprised of one segment which is the color of a positive assay on the carrier matrix. The color panel indicator may also have a segment that is the baseline color of the carrier matrix. Providing color reference standards for comparison will assist the operator in reading the results of the assay.

Some embodiments of the present invention may have two carrier matrices on the solid support. The carrier matrices are not in contact. The matrices contain identical chemical compounds. One matrix is the sample matrix as described above. The sample is applied to the matrix for assay purposes. The other matrix is the control matrix. A control fluid is applied to the control matrix. The control fluid contains fumarase activity. The level of fumarase activity in the control fluid may vary. A positive control fluid will contain a level of fumarase activity equivalent to the fumarase activity in semen having more than about $20 \times 10^6$ motile sperm per milliliter. A negative control fluid will contain a level of fumarase activity equivalent to the fumarase activity in semen having less than about $20 \times 10^6$ motile sperm per milliliter. Application of a control fluid may provide internal positive and negative controls for the assay, depending on the control fluid employed.

Methods for detection of semen samples having a sufficient concentration of motile sperm for fertility are also provided. The methods generally comprise applying the sample to a carrier matrix on a solid support, which carrier matrix contains a fumarase substrate and malate dehydrogenase; and detecting a visual signal from the solid support resulting from metabolism of the fumarase substrate by fumarase present in the sample.

The semen assayed in the present invention will generally be fresh. Following collection, the semen is usually incubated at room temperature for 15-30 minutes. The semen liquifies during the incubation providing easier and more uniform application of the sample to the carrier matrix. When the carrier matrix is mounted on a dipstick, the dipstick is dipped into the sample until the carrier matrix is wetted. If the carrier matrix is not mounted on a dipstick, the sample may be applied to the carrier matrix by a swab, pipette, or the like.

The sample is incubated on the carrier matrix at room temperature. The color of the carrier matrix is assessed at 1, 3, 5, 7, and 10 minutes. A bluish purple color on the pad indicates a positive result. No color change or a very faint color change indicates a negative result. The color of the carrier matrix may be compared to the color reference to assist the operator when making a visual comparison. The color reference may be on a color indicator panel on the solid support or a separate color key. Alternatively, the color of the carrier matrix may be analyzed by an instrument such as a reflectance analyzer or a video image analyzer.

When a control matrix is present on the solid support, the control fluid is applied to the control matrix immediately after application of the sample to the sample matrix. The color of the control matrix is assessed with the color of the sample matrix. When used as a positive control, the control matrix should be a bluish purple color within 10 minutes of application of the control fluid if the assay is performing properly. When used as a negative control, the control matrix should be colorless or only a very faint bluish color when the device is performing properly.

Kits for detection of semen samples having more than about $20 \times 10^6$ motile sperm per milliliter are also provided. The kits include a device of the present invention and a semen collection vial. The shape and composition of the vial is not critical and may vary. A pipette may also be included as appropriate. The kits may also contain vials of control fluids. Both positive and negative control fluids may be included in the kits.

A color key may also be provided in the kits of the present invention. The color key will generally have segments of different colors. Generally, the color key will have bluish purple segments typical of a positive assay and faint bluish segments typical of a negative assay. The kits may also contain a reflectance analyzer or video image analyzer.

The following examples are offered by way of illustration and not of limitation.

EXAMPLE 1

This example demonstrates the construction of a device of the present invention and use of the device for assessing sperm count and sperm motility in patients attending an infertility clinic.

A solution containing sodium fumarate, malic acid, malic dehydrogenase and a dye system coupled to NAD+ was prepared with the following constituents:

|  | Volume |
| --- | --- |
| 1 mM Fumarate | 200 μl |
| 1 mM Malic acid | 50 μl |
| 2.5 mM magnesium chloride | 100 μl |
| MTT (10 mg/ml) | 50 μl |
| NAD (10 mg/ml) | 100 μl |
| Ethoxy PMS (2.5 mg/ml) | 10 μl |
| Malic dehydrogenase | 5 U/10 μl |
| Total Volume | 520 μl |

The solution was diluted 1:5 with deionized water to a final volume of 2.5 ml and mixed with 2.5 ml of 10% gelatin in phosphate buffered saline. Filter paper strips were dipped in the solution and dried at 45° C. in a forced air oven for 15 minutes. The dried filter paper containing the reagents was attached to a piece of plastic using double-faced adhesive tape. The plastic was cut into dipsticks.

The dipsticks were taken to an infertility clinic for office testing of fresh semen samples. Patients supplied samples in the clinic which were allowed to liquify at room temperature for 15-30 minutes. A dipstick was placed in each sample until the reagent pad was wetted. The dipsticks were examined five minutes following application of the sample. Positive reactions were determined by a non-de minimis blue coloration of the reagent pad after five minutes. Negative responses were determined by no color change or a very faint blue tint of the reagent pad after five minutes.

The samples were also assessed microscopically. Experienced laboratory technicians measured both the absolute sperm count and sperm motility by standard methods. The results were compared and are set forth in Table 1 below:

TABLE 1

Data From an Infertility Clinic
Individual Results

| Sample No. | Absolute Concentration (millions) | Motility (%) | Motile Concentration (× 10⁶) | Microscopic Result | Dipstick Result |
|---|---|---|---|---|---|
| 1 | 142.5 | 68 | 97 | + | + |
| 2 | 129.5 | 67 | 87 | + | + |
| 3 | 30.6 | 65 | 20 | + | + |
| 4 | 40.0 | 66 | 26 | + | + |
| 5 | 261.5 | 45 | 118 | + | + |
| 6 | 148.8 | 43 | 64 | + | + |
| 7 | 95.8 | 67 | 64 | + | + |
| 8 | 54.6 | 43 | 23 | + | + |
| 9 | 30.1 | 61 | 18 | + | + |
| 10 | 4.1 | 0 | 0 | − | − |
| 11 | 144.0 | 67 | 97 | + | + |
| 12 | 0.15 | 1 | 0 | − | − |
| 13 | 22.0 | 53 | 12 | + | +/− |
| 14 | 41.3 | 74 | 31 | + | + |
| 15 | 21.9 | 28 | 6 | − | − |
| 16 | 134.0 | 51 | 68 | + | + |
| 17 | 82.3 | 66 | 54 | + | + |
| 18 | 26.3 | 66 | 17 | + | +/− |
| 19 | 46.5 | 70 | 33 | + | + |
| 20 | 104.1 | 66 | 69 | + | + |
| 21 | 55.0 | 75 | 41 | + | + |
| 22 | 240.0 | 67 | 160 | + | + |
| 23 | 312.9 | 65 | 203 | + | + |
| 24 | 161.5 | 67 | 108 | + | + |
| 25 | 78.3 | 44 | 34 | + | + |
| 26 | 106.0 | 75 | 79 | + | + |
| 27 | 15.5 | 16 | 2.5 | − | − |
| 28 | 60.3 | 62 | 37 | + | + |
| 29 | 145.5 | 58 | 84 | + | + |
| 30 | 114.8 | 63 | 72 | + | + |
| 31 | 64.0 | 71 | 54 | + | + |
| 32 | 118.3 | 57 | 67 | + | + |
| 33 | 38.3 | 41 | 16 | + | + |
| 34 | 43.0 | 64 | 28 | + | + |
| 35 | 8.7 | 22 | 2 | − | − |
| 36 | 21.9 | 15 | 3 | − | − |
| 37 | 230.0 | 66 | 151 | + | + |
| 38 | 108.0 | 71 | 77 | + | + |
| 39 | 0.0 | 0 | 0 | − | − |
| 40 | 48.0 | 78 | 37 | + | + |
| 41 | 364.0 | 64 | 232 | + | + |
| 42 | 23.1 | 6 | 1 | − | − |
| 43 | 25.1 | 62 | 15 | + | + |
| 44 | 91.3 | 60 | 54 | + | + |
| 45 | 2.0 | 58 | 1 | − | − |
| 46 | 176.0 | 68 | 119 | + | + |
| 47 | 157.0 | 56 | 87 | + | + |
| 48 | 394.5 | 64 | 252 | + | + |
| 49 | 36.5 | 63 | 22 | + | + |
| 50 | 0.99 | 2 | 0 | − | − |
| 51 | 79.5 | 73 | 58 | + | + |
| 52 | 165.0 | 65 | 107 | + | + |
| 53 | 189.5 | 68 | 128 | + | + |
| 54 | 23.5 | 27 | 6 | − | +/− |
| 55 | 97.0 | 58 | 56 | + | + |
| 56 | 4.1 | 69 | 3 | − | − |
| 57 | 153.0 | 63 | 96 | + | + |
| 58 | 0.0 | 0 | 0 | − | − |
| 59 | 49.0 | 60 | 29 | + | + |
| 60 | 64.8 | 35 | 23 | + | + |
| 61 | 67.5 | 50 | 34 | + | + |
| 62 | 34.9 | 2 | 0 | − | − |
| 63 | 7.4 | 48 | 36 | − | − |
| 64 | 57.5 | 71 | 41 | + | + |
| 65 | 252.5 | 62 | 156 | + | + |
| 66 | 48.6 | 83 | 40 | + | + |
| 67 | 32.3 | 65 | 21 | + | + |
| 68 | 203.0 | 65 | 132 | + | + |
| 69 | 160.3 | 48 | 77 | + | + |
| 70 | 11.6 | 29 | 3 | − | − |
| 71 | 1.1 | 0 | 0 | − | − |
| 72 | 17.3 | 47 | 8 | − | − |
| 73 | 105.5 | 73 | 77 | + | + |
| 74 | 0.6 | 0 | 0 | − | − |
| 75 | 50.0 | 45 | 28 | + | + |
| 76 | 65.6 | 50 | 33 | + | + |
| 77 | 55.0 | 60 | 33 | + | + |
| 78 | 30.0 | 70 | 21 | + | + |
| 79 | 188.0 | 82 | 154 | + | + |
| 80 | 111.5 | 45 | 50 | + | + |
| 81 | 2.5 | 62 | 1.5 | − | − |
| 82 | 45.3 | 65 | 29 | + | + |
| 83 | 3.9 | 36 | 1.4 | − | − |
| 84 | 35.3 | 42 | 15 | + | + |
| 85 | 0.0 | 0 | 0 | − | − |
| 86 | 0.25 | 0 | 0 | − | − |
| 87 | 82.5 | 63 | 52 | + | + |
| 88 | 123.0 | 72 | 89 | + | + |
| 89 | 1.3 | 41 | 0.5 | − | − |
| 90 | 2.5 | 62 | 1.6 | − | − |
| 91 | 19.0 | 42 | 8 | − | +/− |
| 92 | 0.79 | 1 | 0 | − | − |
| 93 | 68.3 | 0 | 0 | − | − |
| 94 | 15.9 | 36 | 6 | − | − |
| 95 | 142.5 | 55 | 78 | + | + |
| 96 | 14.0 | 41 | 6 | − | − |
| 97 | 40.0 | 66 | 26 | + | + |
| 98 | 261.5 | 68 | 179 | + | + |
| 99 | 40.0 | 66 | 26 | + | + |
| 100 | 0.0 | 0 | 0 | − | − |
| 101 | 1.2 | 29 | 0 | − | − |
| 102 | 46.7 | 67 | 31 | + | + |
| 103 | 72.3 | 35 | 25 | + | + |
| 104 | 213.0 | 68 | 145 | + | + |
| 105 | 97.5 | 67 | 65 | + | + |
| 106 | 10.9 | 43 | 5 | − | − |
| 107 | 33.3 | 66 | 22 | + | + |
| 108 | 43.9 | 65 | 29 | + | + |

Total Positive = 73
Total Negative = 31
Borderline = 4
Total # = 108

This example demonstrates that the dipstick was highly sensitive and specific with a correlation of 96%.

EXAMPLE 2

This example demonstrates an assessment of the time required for detection of positive reactions in the assays of the present invention. Most positive reactions were apparent within 5 minutes of applying the samples to the dipsticks.

Fresh semen samples were provided to be assayed. The samples contained varying numbers of sperm and motile sperm. The semen was analyzed by traditional microscopic techniques as described above to determine absolute sperm counts and motility. Dipsticks were constructed as described in Example 1. Following liquefaction of the semen by incubation at room temperature, the dipstick reagent pads were wetted in the samples. The color of the pads was assessed at 1, 3, 5, 7, and 10 minutes following application. The color was scored 0–4+. Zero was no color change and 4+ was a marked color change. A 1+ reading was considered a positive result. The results are set forth in Table 2 below.

TABLE 2

MALE FERTILITY TEST

| Sample | Sperm Count × 10⁶ | Motility | No. of Motile Sperm × 10⁶ | Color Results in Minutes | | | | |
|---|---|---|---|---|---|---|---|---|
| | | | | 1 | 3 | 5 | 7 | 10 |
| SID9230 | 0 | 0% | 0 | — | 0 | 0 | 0 | 0–1 |
| D241 | 267 | 65% | 173.6 | — | 0 | 0–1 | 1 | 2 |
| D283 | 39 | 83,85% | 32.8 | — | 0–1 | 1–2 | 3 | 4 |
| D257 | 94 | 77,78% | 77,78 | 1 | 2 | 2–3 | 3 | 3 |
| SID9233 | 2.4 | 51% | 1.2 | 0 | 0 | 0 | 0 | 0–1 |
| SID9234 | .22 | 8% | .018 | 0 | 0 | 0 | 0–1 | 0–1 |
| SID9240 | 5.5 | 47% | 2.6 | 0 | 0 | 0–1 | 1–2 | 2–3 |
| SID9244 | 4.4 | 25% | 1.1 | 0 | 0 | 1 | 1–2 | 2–3 |
| SID9247 | 4.4 | 40% | 1.8 | 0 | 0 | 0 | 0 | 0 |
| D283 | 6.5 | 79% | 51.4 | 0 | 0–1 | 1 | 2–3 | 3 |
| D275 | 18.2 | 74% | 134.7 | 0 | 1 | 2 | 3 | 3–4 |
| D257 | 43.5 | 77,79% | 33.9 | 0 | 0–1 | 1–2 | 3 | 3 |
| SID9256 | 81 | 59% | 47.8 | 0 | 0–1 | 1 | 2 | 2–3 |
| SID9257 | 4.0 | 46% | 1.84 | 0 | 0 | 0 | 0 | 0 |
| NTW | 15.3 | 64% | 9.8 | 0 | 0 | 0 | 0–1 | 1 |
| SID9259 | 29.8 | 48% | 14.3 | 0 | 0 | 0–1 | 1 | 1–2 |
| SID9263 | 29 | 36% | 10.4 | 0 | 1 | 1–2 | 2 | 2–3 |
| SID9265 | 1.8 | 20% | .36 | 0 | 0 | 0–1 | 1 | 2 |
| SID9266 | 25.8 | 51% | 13.2 | 0 | 0 | 0 | 0 | 0–1 |
| SID9267 | 9.8 | 43% | 4.2 | 0 | 0 | 0 | 0 | 0–1 |
| SID9269 | 36 | 0% | 0 | 0 | 0 | 0 | 0 | 0–1 |
| SID9270 | 17 | 26% | 4.42 | 0 | 0 | 0 | 0 | 1 |
| SID9271 | 0.22 | 11% | 0.02 | 0 | 0 | 0 | 0 | 0 |
| SID9275 | 0 | 0% | 0 | 0 | 0 | 0–1 | 0–1 | 1 |
| SID9284 | 13.7 | 51% | 6.49 | 0 | 0–1 | 1 | 1–2 | 2 |
| SID9283 | 0.5 | 21% | 0.105 | 0 | 0 | 0 | 0 | 0 |
| SID9288 | 5.0 | 39% | 1.95 | 0 | 0 | 0–1 | 1–2 | 2 |
| SP 0248 | 0 | 0% | 0 | 0 | 0 | 0 | 0 | 0 |
| SID9286 | 40 | 56% | 23 | 0 | 0 | 0–1 | 1 | 2 |
| SID9292 | 39.8 | 48% | 19 | 0 | 0 | 0–1 | 1–2 | 2 |
| SP0197629 | 0 | 0% | 0 | 0 | 0 | 0 | 0 | 0–1 |
| SID929 | 40 | 48% | 19 | 0 | 0 | 1 | 2 | 2–3 |

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A device for quantitatively assessing motile sperm in a semen sample, comprising a solid support having an insoluble sample carrier matrix containing a fumarase substrate, malate dehydrogenase, and means for generating a visual signal wherein said fumarase substrate reacts with fumarase in said sample to produce malic acid and said means for generating responds to a reaction between said malate dehydrogenase and malic acid to indicate an amount of motile sperm in the sample.

2. A device as in claim 1, wherein the fumarase substrate is fumaric acid, a fumarate salt, or a fumarate ester.

3. A device as in claim 1, wherein the sample carrier matrix is formed from a material selected from the group consisting of paper, cellulose, synthetic resin fleeces, glass fibers, woven and non-woven fabrics, polystyrene and polypropylene.

4. A device as in claim 1, wherein the mean for generating a visual signal comprises nicotinamide adenine dinucleotide.

5. A device as in claim 4, wherein the sample carrier matrix further contains magnesium chloride, a tetrazolium salt, and phenazine methosulfate.

6. A device as in claim 1, wherein the sample carrier matrix further contains malic acid.

7. A device as in claim 1, wherein the solid support is a dipstick.

8. A device as in claim 7, wherein the dipstick further comprises a color indicator panel.

9. A device as in claim 1, wherein the sample carrier matrix is a porous membrane.

10. A device as in claim 1, further comprising a control carrier matrix, which control carrier matrix contains a fumarase substrate and malate dehydrogenase.

11. A method for identifying a semen sample having more than $20 \times 10^6$ motile sperm per milliliter, said method comprising:

applying the sample to an insoluble carrier matrix on a dipstick solid support, which carrier matrix contains a fumarase substrate, malate dehydrogenase, and a means for generating a visual signal wherein said fumarase substrate reacts with fumarase in said sample to produce malic acid and said means for generating responds to a reaction between said malate dehydrogenase and malic acid to indicate an amount of motile sperm in the sample; and detecting the visual signal from the solid support resulting from metabolism of the fumarase substrate by fumarase present in the sample to determine if the sample contains more than $20 \times 10^6$ motile sperm per milliliter.

12. A method as in claim 11, wherein the means for generating a visual signal comprises NAD+.

13. A method as in claim 11, wherein the semen sample is liquified prior to application to the carrier matrix.

14. A method as in claim 11, wherein the fumarase substrate is fumaric acid, a fumarate salt, or a fumarate ester.

15. A method as in claim 11, wherein the visual signal is a color change on the carrier matrix.

16. A method as in claim 11, wherein the visual signal is detected within 10 minutes of applying the sample to the carrier matrix.

17. A method as in claim 11, further comprising comparing the visual signal detected with a color reference.

18. A method as in claim 17, wherein the visual signal is visually compared with the color reference.

19. A method as in claim 17, wherein the visual signal is compared with the color reference by a reflectance analyzer or a video image analyzer.

20. A method as in claim 11, further comprising applying a control fluid to a control carrier matrix on the solid support and observing a visual signal from the control carrier matrix.

21. A kit for the detection of a semen sample having more than $20 \times 10^6$ motile sperm per milliliter, comprising:

a solid support having an insoluble carrier matrix containing a fumarase substrate, malate dehydrogenase, means for generating a visual signal wherein said fumarase substrate reacts with fumarase in said sample to produce malic acid and said means for generating responds to a reaction between said malate dehydrogenase and malic acid to indicate an amount of motile sperm in the sample, and a semen collection vial.

22. A kit as in claim 21, wherein the means for generating a visual signal comprises nicotinamide adenine dinucleotide.

23. A kit as in claim 21, further comprising a reference color chart, a reflectance analyzer, or a video image analyzer.

24. A kit as in claim 21, wherein the fumarase substrate is fumaric acid, a fumarate salt, or a fumarate ester.

25. A kit as in claim 21, wherein the solid support is a dipstick.

26. A kit as in claim 21, wherein the carrier matrix further comprises magnesium chloride, nicotinamide adenine dinucleotide, a tetrazolium salt, and phenazine methosulfate.

27. A kit as in claim 21, further comprising a control fluid.

* * * * *